(12) United States Patent
Cernatescu et al.

(10) Patent No.: US 10,161,887 B2
(45) Date of Patent: Dec. 25, 2018

(54) SYSTEMS AND METHODS FOR MATERIALS ANALYSIS

(71) Applicant: UNITED TECHNOLOGIES CORPORATION, Farmington, CT (US)

(72) Inventors: Iuliana Cernatescu, Glastonbury, CT (US); Vasisht Venkatesh, West Hartford, CT (US); David Ulrich Furrer, Marlborough, CT (US)

(73) Assignee: UNITED TECHNOLOGIES CORPORATION, Farmington, CT (US)

( * ) Notice: Subject to any disclaimer, the term of this patent is extended or adjusted under 35 U.S.C. 154(b) by 118 days.

(21) Appl. No.: 14/600,511

(22) Filed: Jan. 20, 2015

(65) Prior Publication Data

US 2016/0209340 A1 Jul. 21, 2016

(51) Int. Cl.
*G01N 23/207* (2018.01)
*G01N 23/20016* (2018.01)

(52) U.S. Cl.
CPC ..... *G01N 23/207* (2013.01); *G01N 23/20016* (2013.01); *G01N 2223/605* (2013.01); *G01N 2223/606* (2013.01); *G01N 2223/632* (2013.01)

(58) Field of Classification Search
CPC . G01N 23/20; G01N 23/20016; G01N 23/207
See application file for complete search history.

(56) References Cited

U.S. PATENT DOCUMENTS

| 3,636,347 | A | 1/1972 | Poot |
| 5,148,458 | A | 9/1992 | Ruud |
| 6,118,850 | A | 9/2000 | Mayo et al. |
| 6,385,289 | B1 * | 5/2002 | Kikuchi ............... G01N 23/20 378/70 |
| 7,158,609 | B2 * | 1/2007 | Kikuchi ............... G01N 23/205 378/70 |

(Continued)

FOREIGN PATENT DOCUMENTS

| DE | 4236291 A1 | 4/1994 |
| EP | 1193492 A1 | 4/2002 |
| EP | 1947448 A1 | 7/2008 |

OTHER PUBLICATIONS

X-Ray Diffraction Imaging (X-ray topography) http://esrf.eu/UsersAndScience/Experiments/Imaging/ID19/Techniques/Diffraction/Overview/.

(Continued)

*Primary Examiner* — Wyatt Stoffa
(74) *Attorney, Agent, or Firm* — Cantor Colburn LLP

(57) ABSTRACT

A system for the x-ray topography analysis of a sample, comprising in combination, a goniometer having a base, a tube arm rotatably associated with the base, a detector arm rotatably associated with the base, and a sample stage operatively associated with the base. The system also includes an x-ray source operatively coupled with the tube arm and is capable of emitting a non-collimated beam of x-rays. A collimator is operatively associated with the x-ray source and converts the non-collimated beam of x-rays into a collimated beam of x-rays having a quasi-rectangular shape with a divergence less than three degrees in all directions. A detector operatively coupled to the detector arm.

13 Claims, 3 Drawing Sheets

(56) References Cited

U.S. PATENT DOCUMENTS

| | | | |
|---|---|---|---|
| 7,269,245 B2* | 9/2007 | He | G01N 23/20 356/301 |
| 7,535,992 B2* | 5/2009 | Taguchi | G01N 23/207 378/124 |
| 7,848,489 B1 | 12/2010 | He et al. | |
| 8,322,221 B1 | 12/2012 | Sathish et al. | |
| 8,548,123 B2* | 10/2013 | He | G01N 23/207 378/71 |
| 2003/0068010 A1* | 4/2003 | Lentfer | G01N 23/20016 378/81 |
| 2004/0017896 A1* | 1/2004 | Hajduk | B01J 19/0046 378/208 |
| 2005/0078790 A1* | 4/2005 | Kikuchi | G01N 23/205 378/73 |
| 2006/0023838 A1* | 2/2006 | He | G01N 23/20016 378/81 |
| 2006/0093090 A1* | 5/2006 | He | G01N 23/207 378/70 |
| 2007/0003012 A1* | 1/2007 | Taguchi | G01N 23/207 378/71 |
| 2007/0019788 A1* | 1/2007 | Ledoux | G01N 23/04 378/88 |
| 2008/0031416 A1* | 2/2008 | Dosho | G01N 23/20 378/81 |
| 2008/0159479 A1* | 7/2008 | Huang | G01N 23/20 378/73 |
| 2011/0268251 A1* | 11/2011 | He | G01N 23/207 378/71 |
| 2012/0140890 A1* | 6/2012 | Ozawa | G01N 23/207 378/74 |
| 2013/0259200 A1* | 10/2013 | Omote | G01N 23/207 378/74 |
| 2014/0260623 A1* | 9/2014 | Salem | G01N 23/20 73/584 |
| 2015/0085983 A1* | 3/2015 | Harding | G01N 23/201 378/87 |
| 2015/0253262 A1* | 9/2015 | Cernatescu | G01N 23/207 378/73 |
| 2016/0266056 A1* | 9/2016 | Ruth | G01N 23/207 |

OTHER PUBLICATIONS

X-Rat Topography, David R. Black, Grabrielle G. Long: www.ceramics.nist.gov/ftproot/xraytop.pdf.

European Search Report for Application No. 16152126.5; dated May 27, 2016.

Pilchak, Adam L. et al., "A Quantitative Assessment of Microtexture in Titanium Alloys using Destructive and Nondestructive Methods", Microscopy and Microanalysis, vol. 20, No. S3, Aug. 27, 2014, pp. 1448-1449.

* cited by examiner

SYSTEMS AND METHODS FOR MATERIALS ANALYSIS

FIELD OF THE DISCLOSURE

This disclosure generally relates to systems and methods for the analysis of samples and, more specifically, to x-ray topography systems and methods for the analysis of samples.

BACKGROUND OF THE DISCLOSURE

Elemental titanium is an allotropic material. With proper conditioning, a sample of elemental titanium exists as a hexagonal close-packed (HCP) crystalline phase at ambient temperatures and pressures referred to as the alpha-phase. When the temperature of such sample is increased to around 890 degrees Celsius, a body-centered cubic (BCC) crystalline phase begins to form that remains stable to titanium's melting temperature of 1668 degrees Celsius. This BCC phase is known as the beta-phase. Alloying elements, such as aluminum or germanium, may be added to such sample to increase or depress its alpha-to-beta phase transition temperature. However, the alpha-phase and beta-phase crystalline phases always coexist to some degree if such sample is heated to or above a certain temperature coinciding with its alpha-to-beta phase transition temperature. When a sample contains both alpha and beta phases, it is referred to as dual-phase titanium.

Literature reports that dual-phase titanium alloy samples are susceptible to the formation of a beta-phase interspersed with large, commonly oriented regions of alpha-phase particles known as micro-textured regions (MTR). While not conclusive, literature suggests that the formation of such MTRs may lead to a reduction in such samples' fatigue life during dwell loading. Literature additionally proposes that this reduction occurs when the samples are exposed to temperatures less than or equal to about 200 degrees Celsius when coupled with a stress level of 0.60 of the samples' yield strength.

Different systems, such as X-ray crystallography machines, exist that can confirm the presence MTRs. However, such systems are not designed to characterize and quantify the shape, size, density and orientation of MTRs in samples. Instead, X-ray topography systems are better suited to undertake such analyses. Yet, X-ray topography systems are not without their limitations. Known X-ray topography systems may incorporate the necessary resolution to characterize and quantify the shape, size, density and orientation of MTRs in samples, but are best suited for use in a low-throughput, research-based environment. Other known X-ray topography systems include the speed necessary for a manufacturing environment, but lack the resolution necessary to characterize and quantify the shape, size, density and orientation of MTRs in samples. Thus a need exists for an X-ray topography system that combines the resolution found in research-based machinery with the greater speed necessary for manufacturing environments. The present disclosure is directed toward this end.

SUMMARY OF THE DISCLOSURE

In accordance with one aspect of the present disclosure, a system for the x-ray topography analysis of a sample is disclosed. The system may include a goniometer having a base, a tube arm rotatably associated with the base, a detector arm rotatably associated with the base and a sample stage operatively associated with the base. The system may further include an x-ray source that is operatively coupled with the tube arm and capable of emitting a non-collimated beam of x-rays and a collimator operatively associated with the x-ray source. The collimator may be capable of converting the non-collimated beam of x-rays into a collimated beam of x-rays having a quasi-rectangular shape with a divergence less than three degrees in all directions. A detector may be operatively coupled to the detector arm.

In a refinement of the system for the x-ray topography analysis of a sample, the system, the sample stage may further include one to three axes of translation.

In another refinement of the system for the x-ray topography analysis of a sample, the sample stage may translate in one hundred micrometer increments.

In another refinement of the system for the x-ray topography analysis of a sample, the sample stage may further include one to three axes of rotation.

In another refinement of the system for the x-ray topography analysis of a sample, the sample stage may rotate in one hundred micrometer increments.

In another refinement of the system for the x-ray topography analysis of a sample, the detector may be an area detector including a plurality of pixels.

In another refinement of the system for the x-ray topography analysis of a sample, each of the plurality of pixels may have a detection surface having a width between one micrometer and one thousand micrometers.

In another refinement of the system for the x-ray topography analysis of a sample, the detector may have a detector surface and the detector arm may be an automated detector arm capable of varying the distance between the detector surface and the sample, or an angle between the collimated beam of x-rays and the detector surface.

In another refinement of the system for the x-ray topography analysis of a sample, the tube arm and detector arm may be rotatable with respect to the base so that the angle between the collimated beam of x-rays and a diffracted beam of x-rays may vary between zero degrees and one hundred and seventy degrees.

In another refinement of the system for the x-ray topography analysis of a sample, the detector may be in electrical communication with a computer capable of analyzing an output signal of the detector.

In accordance with another aspect of the present disclosure, an X-ray diffraction system for the characterization of micro-textured regions in a metal sample containing more than one crystalline phase is disclosed. The system may include a goniometer having a base, an automated tube arm rotatably associated with the base, an automated detector arm rotatably associated with the base, and an automated sample stage operatively associated with the base. The system may also include an x-ray source that radiatively supplies an array of non-collimated x-rays coupled to the automated tube arm. A collimator may also be included that is operatively associated with and downstream of the x-ray source, the collimator providing a beam of x-rays that has a divergence in all directions less than or about equal to three degrees. A pixelated area detector may be coupled to the automated detector arm. The detector may have a plurality of pixels that extend in a first direction from a point and extend in a second direction from the point, each pixel having a detection surface having a width between one micrometer and one thousand micrometers and the detector may generate an output signal. Finally, a computer may be in electrical communication with the goniometer and contain a first algorithm that controls the movement of the automated tube arm, the automated detector arm and the automated stage.

In a refinement of the X-ray diffraction system for the characterization of micro-textured regions in a metal sample containing more than one crystalline phase the output signal may be sent to the computer and the computer comprises a second algorithm that quantifies shape, size, density and orientation of the micro-textured regions in the sample based on the output signal.

In another refinement of the X-ray diffraction system for the characterization of micro-textured regions in a metal sample containing more than one crystalline phase, the automated stage may also include three axes of translation, three axes of rotation and the first algorithm translates and rotates the stage in one hundred micrometer increments.

In another refinement of the X-ray diffraction system for the characterization of micro-textured regions in a metal sample containing more than one crystalline phase, the first algorithm may vary the distance between the sample and the pixelated detector by moving the automated detector arm.

In another refinement of the X-ray diffraction system for the characterization of micro-textured regions in a metal sample containing more than one crystalline phase the automated tube arm and automated detector arm may be rotatable with respect to the base, and the first algorithm may rotate these arms with respect to the base so that the angle between beam of x-rays and a diffracted beam of x-rays varies between zero degrees and one hundred and seventy degrees.

In accordance with another aspect of the present disclosure, a method for the characterization of micro-textured regions in a metal sample containing more than one crystalline phase is disclosed. The method may include a first step of providing an x-ray diffraction system having a sample stage that includes three axes of translation and three axes of rotation, an x-ray source, a collimator that provides a collimated beam of x-rays with a divergence less than three degrees in all directions, a pixelated area detector whose distance between it and the sample stage is variable, and wherein the angle between the X-ray source and the pixelated area detector may be varied between zero degrees and one hundred and seventy degrees. In a next step, the pixelated area detector may be turned on and the detector may continuously create an output signal. In a next step, the X-ray source may be turned on. Then, the sample stage, X-ray source and the detector may be moved until a portion of the collimated beam of X-rays is diffracted from the metal sample into the detector. Finally, the output signal may be sent to a computer.

In a refinement of the method for the characterization of micro-textured regions in a metal sample containing more than one crystalline phase, the method of claim 16, the moving of the sample stage is translation and the method may further include the step of translating the sample stage in one hundred micrometer increments along all three axes of translation.

In another refinement of the method for the characterization of micro-textured regions in a metal sample containing more than one crystalline phase, the computer quantifies the shape, size, density and orientation of the micro-textured regions in the sample.

In another refinement of the method for the characterization of micro-textured regions in a metal sample containing more than one crystalline phase, the moving of the sample stage is rotation and the method may include the step of rotating the sample stage in one hundred micrometer increments along one axis of rotation.

In another refinement of the method for the characterization of micro-textured regions in a metal sample containing more than one crystalline phase, the computer quantifies the shape, size, density and orientation of the micro-textured regions in the sample.

These and other aspects and features of the present disclosure will be more readily understood when read in conjunction with the accompanying drawings.

DETAILED DESCRIPTION OF THE DISCLOSURE

Figure 1:
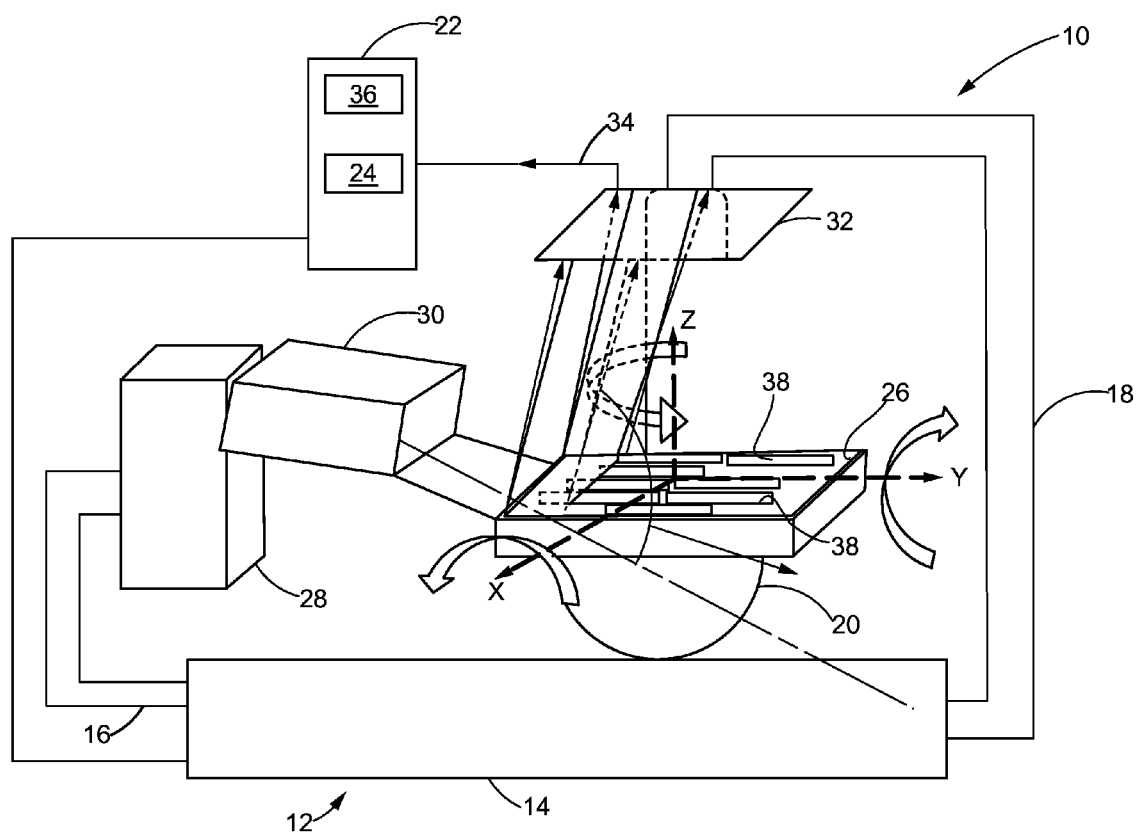
FIG. 1 is a side elevation view of an X-ray diffraction system for the characterization of micro-textured regions in a metal sample containing more than one crystalline phase constructed in accordance with the present disclosure.

Referring now to the drawings, and with specific reference to FIG. 1, an X-ray diffraction system for the characterization of micro-textured regions in a metal sample containing more than one crystalline phase constructed in accordance with the present disclosure is generally referred to by reference numeral 10. The X-ray diffraction system includes a goniometer 12 having a base 14, a tube arm 16 rotatably associated with the base 14, a detector arm 18 rotatably associated with the base 14 and a sample stage 20 operatively associated with the base 14.

The X-ray diffraction system 10 may further include a computer 22. This computer 22 may be in electrical communication with the goniometer 12 and include a first algorithm 24. The first algorithm 24 may control the movement of the tube arm 16, the detector arm 18 and the sample stage 20. Accordingly, the movement of the tube arm 16, the detector arm 18 and sample stage 20 may be automated by their interaction with the computer 22.

The tube arm 16 may rotate around the base 14 between an angle of zero degrees and one hundred seventy degrees. Like the tube arm 16, the detector arm 18 may also rotate around the base 14 between an angle of zero degrees and one hundred and seventy degrees. The arms 16, 18 are rotatable around the base 14 so that a sample 26 may be analyzed from multiple locations.

Still referring to FIG. 1, the X-ray diffraction system further comprises an X-ray source 28 that is operatively coupled to the tube arm 16. Since the X-ray source 28 is coupled to the tube arm 16, the movement of the source 28 coincides with the automated movement of the arm 16. This X-ray source 28 is capable of radiatively supplying an array of non-collimated x-rays. While not all inclusive, examples of an x-ray source 28 that may be used with this system include a copper target, molybdenum target, nickel target, titanium target and silver target sources.

A collimator 30 may be operatively associated with and located downstream of the X-ray source 28. As the X-rays from the source 28 pass through the collimator 30, the array of non-collimated X-rays may be converted into a collimated beam of x-rays. In one embodiment, this collimated beam may have a quasi-rectangular shape with a divergence less than three degrees in all directions. In another embodiment, this collimated beam may have a quasi-rectangular shape with a divergence less than two degrees in all directions. In a further embodiment, this collimated beam may have a quasi-rectangular shape with a divergence less than one degree in all directions. While not meant to be exhaustive, collimator 30 that may be used with a system 10 constructed in accordance with the present disclosure include slits and X-ray lenses on optical fibers.

This X-ray diffraction system may further include a detector 32 that is operatively coupled to the detector arm 18. Since the detector 32 is coupled to the detector arm 18, the movement of the detector 32 coincides with the automated movement of the detector arm 18. Additionally, the tube arm 18 may also move so that the distance between the sample 26 and the detector 32 is adjustable. This movement allows for focusing of the detector 32 with respect to the sample 26 when the system 10 is in operation.

The detector 32 may be a pixelated area detector that comprises a plurality of pixels that extend in a first direction from a point, and the plurality of pixels may also extend in a second direction from the same point thereby generating an area of pixels. Each pixel of this detector 32 may act as an individual detector having a detection surface, and the width of each detection surface may be between one micrometer and one thousand micrometers. In one instance, the detector 32 may be a charge-coupled device. In another instance, a detector 32 that may be used with this system 10 is an active pixel sensor. In yet other examples, the detector 32 may be a scintillation detector, Xe-field detector or even a solid-state detector.

The detector 32 may generate an output signal 34. This output signal 34 may then be sent to the computer 22 that comprises a second algorithm 36 that is utilized to characterize the sample 26 for the presence of micro-textured regions 38. The second algorithm 36 may further quantify the shape, size, density and orientation of any micro-textured regions 38 present in the sample 26. Limits may be set on the shape, size, density and orientation of any micro-textured regions 38 in the sample 26, and the computer 22 may provide a report whether the sample 26 falls below such limits.

If the system 10 is utilized in a manufacturing environment, then the computer 22 may be pre-loaded with multiple first algorithms 24 based on the shape of the sample 26 such as by Computer Aided Design (CAD) drawings. Then, when a sample 26 having a particular shape is loaded onto the system 10, a first algorithm 24 specific to the shape of the sample 26 may be utilized to control the movement of the tube arm 16, detector arm 18 and the sample stage 20.

Figure 2:
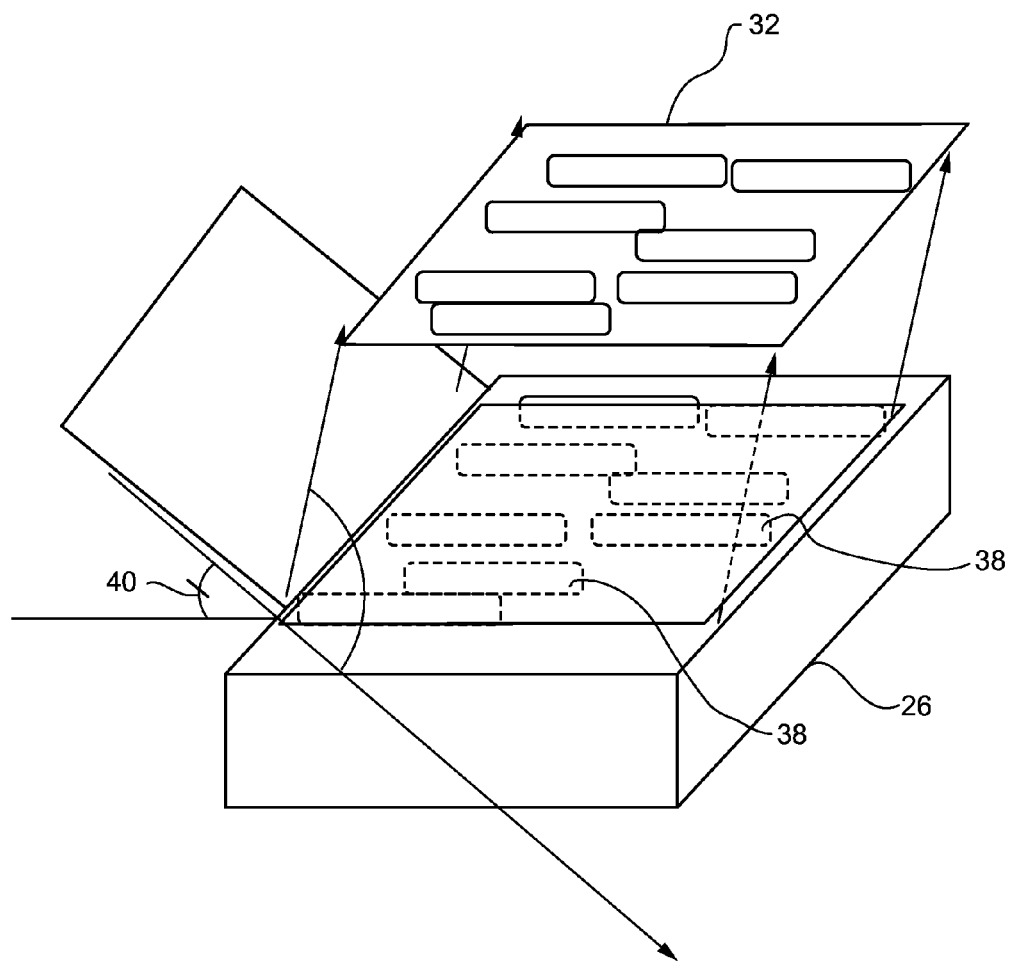
FIG. 2 is a partial isometric side view depicting the operation of the diffraction-detection portion of X-ray diffraction system of FIG. 1.

The operation of the diffraction-detection portion of the X-ray diffraction system manufactured in accordance with the present disclosure is depicted in FIG. 2. As seen there, the collimated beam of X-rays is emitted upon the sample 26. Then, the incoming angle 40 of collimated beam of X-rays with respect to a surface of the sample 26 is adjusted until a portions of the X-rays diffract away from, rather than transmitting through, the sample 26. These diffracted X-rays will be captured by the detector 32. More specifically, the sample 26 will diffract X-rays in locations where micro-textured regions 38 are present. The capture of diffracted X-rays by the detector 32 confirms the presence of these micro-textured regions in the sample 26 under analysis.

Figure 3:
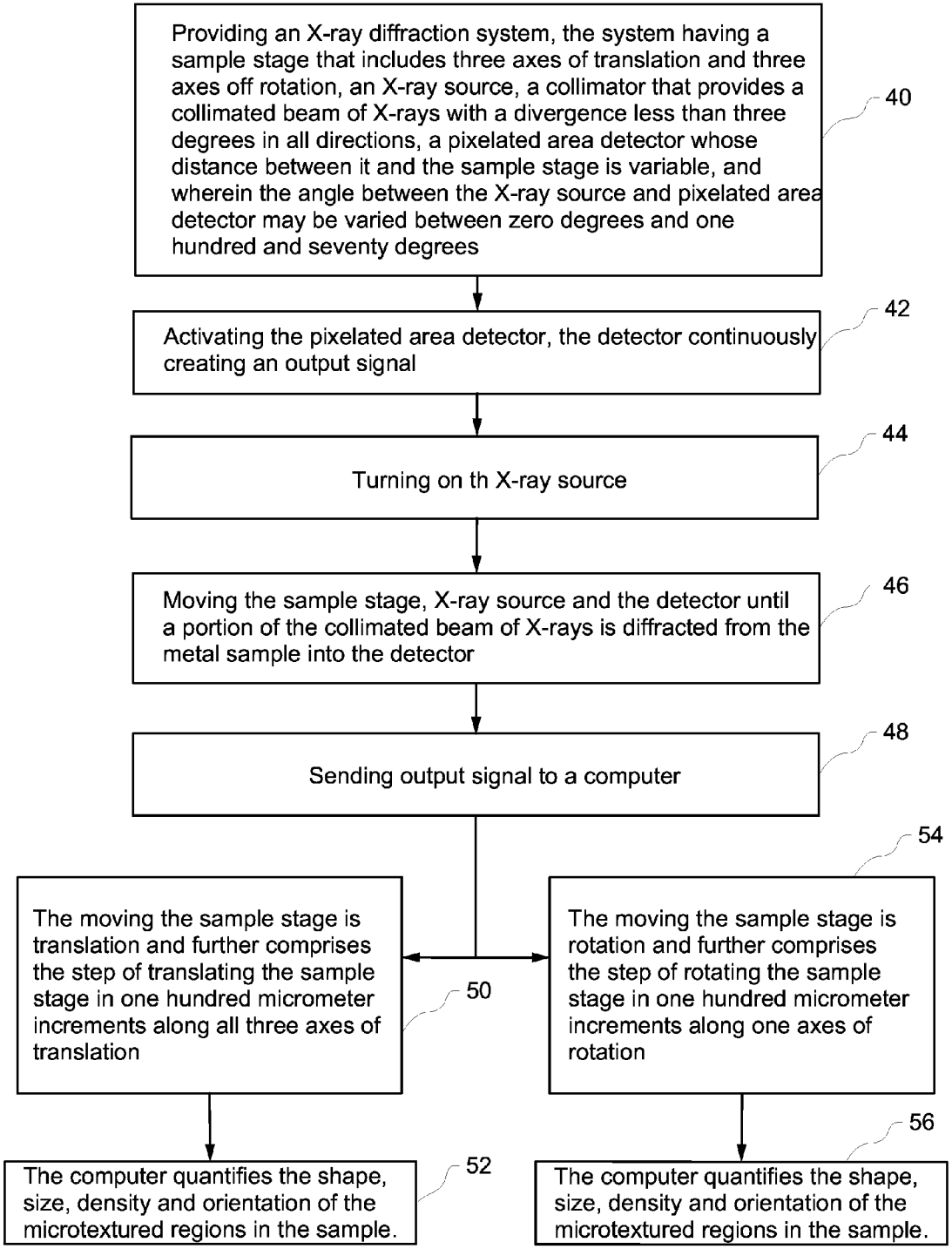
FIG. 3 is a flowchart depicting an exemplary method for the characterization of micro-textured regions in a metal sample containing more than one crystalline phase utilizing a system depicted in FIG. 1.

Referring next to FIG. 3, steps of a method for the characterization of micro-textured regions in a metal sample containing more than one crystalline phase are illustrated. At a step 40, an x-ray diffraction system, the system having a sample stage that includes three axes of translation and three axes of rotation, an x-ray source, a collimator that provides a collimated beam of x-rays with a divergence less than three degrees in all directions, a pixelated area detector whose distance between it and the sample stage is variable, and wherein the angle between the X-ray source and the pixelated area detector may be varied between zero degrees and one hundred and seventy degrees is provided. At a step 42, the pixelated detector is activated and continuously creates an output signal. At a step 44, the X-ray source is turned on. At a step 46, the sample stage, the X-ray source and the detector are moved until a portion of the collimated beam of X-rays is diffracted from the metal sample into the detector. At a step 48, the output signal is sent to a computer.

If the moving the sample stage is translation, then at a step 50, the method further comprises the step of translating the sample stage in one hundred micrometer increments along three axes of rotation. If the moving the sample stage is translation, then at a step 52, the method further includes the computer quantifying the shape, size, density and orientation of the micro-textured regions in the sample.

If the moving the sample stage is rotation, then at a step 54, the method further comprises the step of rotating the sample stage in one hundred micrometer increments along one axis of rotation. If the moving the sample stage is rotation, then at a step 56, the method further includes the computer quantifying the shape, size, density and orientation of the micro-textured regions in the sample.

INDUSTRIAL APPLICABILITY

In operation, the X-ray diffraction system for the characterization of micro-textured regions in a metal sample containing more than one crystalline phase can find use in many industrial settings, such as in a manufacturing environment. More specifically, such a system finds use as a quality control tool in the manufacturing processes of aerospace component manufacturers, such as in the manufacture of gas turbine engines. Such a system includes a goniometer having a base, an automated tube arm rotatably associated with the base, an automated detector arm rotatably associated with the base, and an automated sample stage operatively associated with the base. The system may also include an x-ray source that radiatively supplies an array of non-collimated x-rays coupled to the automated tube arm. A collimator may also be included that is operatively associated with and downstream of the x-ray source, the collimator providing a beam of x-rays that has a divergence in all directions less than or about equal to three degrees. A pixelated area detector may be coupled to the automated detector arm. The detector may have a plurality of pixels that extend in a first direction from a point and extend in a second direction from the point, each pixel having a detection surface having a width between one micrometer and one thousand micrometers and the detector may generate an output signal. Finally, a computer may be in electrical communication with the goniometer and contain a first algorithm that controls the movement of the automated tube arm, the automated detector arm and the automated stage. The computer may also comprise a second algorithm that quantifies the shape, size, density and orientation of micro-textured regions in sample.

The above description is meant to be representative only, and thus modifications may be made to the embodiments described herein without departing from the scope of the disclosure. Thus, these modifications fall within the scope of present disclosure and are intended to fall within the appended claims.

What is claimed is:

1. A system for the x-ray topography analysis of a sample, comprising:
    a goniometer, the goniometer having a base, a tube arm rotatably associated with the base, a detector arm rotatably associated with the base, and a sample stage operatively associated with the base, the sample stage in operation supports a sample;
    an x-ray source, the x-ray source operatively coupled with the tube arm and capable of emitting a non-collimated beam of x-rays;
    a collimator operatively associated with the x-ray source, the collimator capable of converting the non-collimated beam of x-rays into a collimated beam of x-rays having a quasi-rectangular shape with a divergence less than one degree in all directions, wherein the collimated beam of x-rays is directed towards a surface of the sample at an angle of incidence relative to the surface of the sample; and
    a detector operatively coupled to the detector arm; wherein the detector has a detector surface and the detector arm is an automated detector arm capable of varying the distance between the detector surface and the sample and an angle between the collimated beam of x-rays and the detector surface; wherein the detector captures quasi-parallel x-rays diffracted off the surface of the sample at an angle of reflection relative to the surface of the sample; wherein the angle of reflection is different from the angle of incidence; and wherein the detector is located at the angle of reflection.

2. The system of claim 1, wherein the stage further includes one to three axes of translation.

3. The system of claim 2, wherein the stage translates in one hundred micrometer increments.

4. The system of claim 1, wherein the stage further includes one to three axes of rotation.

5. The system of claim 4, wherein the stage rotates in one hundred micrometer increments.

6. The system of claim 1, wherein the detector is an area detector including a plurality of pixels.

7. The system of claim 6, wherein each of the plurality of pixels has a detection surface having a width between one micrometer and one thousand micrometers.

8. The system of claim 1, wherein the tube arm and detector arm are rotatable with respect to the base so that the angle between the collimated beam of x-rays and a diffracted beam of x-rays may vary between zero degrees and one hundred and seventy degrees.

9. The system of claim 1, wherein the detector is in electrical communication with a computer capable of analyzing an output signal of the detector.

10. An X-ray diffraction system for the characterization of micro-textured regions in a metal sample containing more than one crystalline phase, comprising:
    a goniometer, the goniometer having a base, an automated tube arm rotatably associated with the base, an automated detector arm rotatably associated with the base, and an automated sample stage operatively associated with the base, the sample stage in operation supports a sample;
    an x-ray source, the x-ray source coupled to the automated tube arm, the x-ray source radiatively supplying an array of non-collimated x-rays;
    a collimator, operatively associated with and downstream of the x-ray source, the collimator providing a beam of x-rays that has a divergence in all directions less than or about equal to one degree, wherein the collimated beam of x-rays is directed towards a surface of the sample at an angle of incidence relative to the surface of the sample;
    a pixelated detector coupled to the automated detector arm, the detector having a plurality of pixels that extend in a first direction from a point and extend in a second direction from the point, each pixel having a detection surface having a width between one micrometer and one thousand micrometers, the detector generating an output signal;
    a computer in electrical communication with the goniometer having a first algorithm that controls the movement of the automated tube arm, the automated detector arm and the automated stage;
    wherein the detector has a detector surface and the detector arm is an automated detector arm capable of varying the distance between the detector surface and the sample and an angle between the collimated beam of x-rays and the detector surface;
    wherein the detector captures quasi-parallel x-rays diffracted off the surface of the sample at an angle of reflection relative to the surface of the sample;
    wherein the angle of reflection is different from the angle of incidence; and
    wherein the detector is located at the angle of reflection.

11. The system of claim 10, wherein the automated stage further includes three axes of translation, three axes of rotation and the first algorithm translates and rotates the stage in one hundred micrometer increments.

12. The system of claim 10, wherein the first algorithm varies distance between the sample and the pixelated detector by moving the automated detector arm.

13. The system of claim 10, wherein the automated tube arm and automated detector arm are rotatable with respect to the base, and the first algorithm rotates these arms with respect to the base so that the angle between beam of x-rays and a diffracted beam of x-rays varies between zero degrees and one hundred and seventy degrees.

* * * * *